United States Patent
Muller et al.

(10) Patent No.: US 10,919,838 B2
(45) Date of Patent: Feb. 16, 2021

(54) PRODUCTION OF TRI-METHYL BENZENE DERIVATIVES

(71) Applicant: RHODIA OPERATIONS, Paris (FR)

(72) Inventors: Eric Muller, Lyons (FR); Bala N. S Thota, Gujarat (IN)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 16/622,565

(22) PCT Filed: Jun. 14, 2018

(86) PCT No.: PCT/EP2018/065904
§ 371 (c)(1),
(2) Date: Dec. 13, 2019

(87) PCT Pub. No.: WO2018/229237
PCT Pub. Date: Dec. 20, 2018

(65) Prior Publication Data
US 2020/0216382 A1    Jul. 9, 2020

(30) Foreign Application Priority Data
Jun. 14, 2017 (EP) .................................... 17305725

(51) Int. Cl.
C07D 493/08 (2006.01)
C07C 209/48 (2006.01)
C07C 211/49 (2006.01)
C07D 407/10 (2006.01)

(52) U.S. Cl.
CPC .......... C07C 209/48 (2013.01); C07C 211/49 (2013.01); C07D 407/10 (2013.01); C07D 493/08 (2013.01)

(58) Field of Classification Search
CPC ............................ C07D 407/10; C07D 493/08
USPC ......................................................... 549/448
See application file for complete search history.

(56) References Cited

U.S. PATENT DOCUMENTS

| 2,405,267 | A | 8/1946 | Nudenberg |
| 9,718,755 | B2 * | 8/2017 | Sookraj .................. C07C 51/09 |
| 2004/0054219 | A1 | 3/2004 | Nagao et al. |
| 2011/0112323 | A1 | 5/2011 | Kawai et al. |
| 2016/0264506 | A1 | 9/2016 | Hayes et al. |

FOREIGN PATENT DOCUMENTS

| WO | 2010151346 A1 | 12/2010 |
| WO | 2013040514 A1 | 3/2013 |
| WO | 2013048248 A1 | 4/2013 |
| WO | 2014065657 A1 | 5/2014 |
| WO | 2014197195 A2 | 12/2014 |
| WO | 2017096559 A1 | 6/2017 |

OTHER PUBLICATIONS

Cheng, Y-T et al., "Production of targeted aromatics by using Diels-Alder classes of reactions with furans and olefins over ZSM-5", Green Chemistry (2012) vol. 14, Issue 11, pp. 3114-3125.
Hansen, T.S. et al., "Cu catalyzed oxidation of 5-hydroxymethylfurfural to 2,5-diformylfuran and 2,5-furandicarboxylic acid under benign reaction conditions", Applied Catalysis A: General (2013) vol. 456, pp. 44-50.

* cited by examiner

*Primary Examiner* — Niloofar Rahmani

(57) ABSTRACT

The present invention relates to the production of tri-functional aromatic molecules from diformylfuran, in particular to the production of tri-methyl benzene derivatives such as for example trimellitic acid or 1,2,4-tri(aminomethyl)benzene from diformylfuran and its derivatives.

5 Claims, No Drawings

PRODUCTION OF TRI-METHYL BENZENE DERIVATIVES

This application is a U.S. national stage entry under 35 U.S.C. § 371 of International Application No. PCT/EP2018/065904 filed Jun. 14, 2018, which claims priority to European application No. 17305725.8 filed on Jun. 14, 2017 The entire contents of these applications are explicitly incorporated herein by this reference.

The present invention relates to the production of trifunctional aromatic molecules from diformylfuran, in particular to the production of tri-methyl benzene derivatives, such as for example trimellitic acid or 1,2,4-tri(aminomethyl)benzene, from diformylfuran and its derivatives. The invention describes new routes for converting diformylfuran and its derivatives into tri-methylbenzene derivatives including novel intermediates.

In recent times, a tendency has grown to obtain a variety of chemicals from renewable sources. In this context, there has been a tendency to create chemicals from biomass carbohydrates, such as cellulose, starch, hemicellulose, sugars and the like. Under dehydration conditions, these carbohydrates can be converted into a number of interesting chemicals, including furfural, hydroxymethyl furfural and derivatives thereof. There is an interest to use these chemicals for the production of value-added chemical compounds. Examples of such value-added chemical compounds include phthalic acid, terephthalic acid, isophthalic acid, trimellitic acid, hemimellitic acid, pyromellitic acid and other benzene derivatives that contain two or more carboxylic moiety substituents.

One approach to transfer furan, furfural and their derivatives into chemically more valuable six-membered ring aromatic compounds is the Diels-Alder reaction between the furan ring system and ethylene or ethylene derivatives.

The Diels-Alder reaction with furan derivatives is known. The Diels-Alder reaction of furan and ethylene to 3,6-epoxycyclohexene has been described in U.S. Pat. No. 2,405,267:

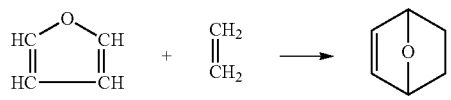

WO 2010/151346 describes the conversion of 2,5-dimethylfuran to para-xylene.

A process for the preparation of a substituted benzene derivative by reacting a furfuryl ether with an ethylene derivative is described in WO 2013/048248.

WO 2014/065657 broadly claims a process for the preparation of benzene derivatives by reacting a furan derivative with ethylene. The furan derivative may bear at 2 and 5 position a variety of substituents including alkyl, aralkyl, —CHO, —CH$_2$OR$^3$, —CH(OR$^4$)(OR$^5$) and —COOR$^6$. However, this document provides examples only with 2,5-dimethylfuran, 2-methylfuran, 2,5-furan dicarboxylic acid and the dimethylester of 2,5-furan dicarboxylic acid. In particular, there is no example wherein furfural is converted into a benzene derivative.

Yu-Ting Cheng, et al. in Green Chem., 2012, 14, 3314-3325 provide an overview over the production of targeted aromatics by using Diels-Alder classes of reactions with furans and olefins. The authors found that while furan, methylfuran and dimethylfuran react smoothly with olefins, the first step for furfural conversion is decarbonylation to form furan and CO. The produced furan then enters the known furan conversion reaction:

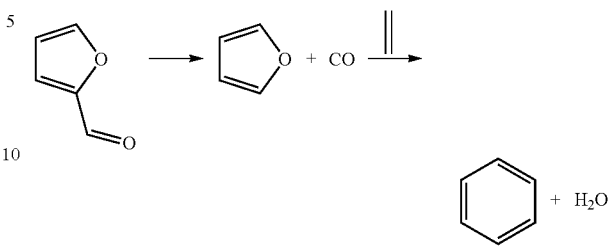

These difficulties in reacting furfural with olefins are confirmed in WO 2014/197195. Although the authors of this document conducted screening experiments, testing range of various solvents, catalysts, reaction temperatures, pressures and times, and 5-hydroxy-2-furfural concentrations, they failed to identify a system in which 4-hydroxymethylbenzaldehyde is formed. The authors suggest solving this problem by air oxidation of 5-hydroxymethyl-2-furfural to generate the corresponding 5-hydroxymethyl-2-furoic acid or other oxidized derivative, which has been shown to work well in the Diels-Alder reaction with olefins.

Both, decarbonylation of furfural to furan as well as oxidation of furfural to furoic acid has the disadvantage that the aldehyde substituent at the furan ring is lost. As a consequence thereof, the aldehyde substituent is no longer present in the obtained Diels-Alder adduct which makes it more difficult to obtain benzaldehyde derivatives from furan derivatives and in particular furfural. However, benzaldehyde derivatives are desirable as valuable intermediates in the preparation of other important chemical compounds, such as meta-xylenediamine, ortho-xylenediamine and 1,2,3-tri(aminomethyl)benzene. In addition to these compounds, 1,2,4-trimethyl benzene derivatives, such as trimellitic acid or 1,2,4 tri(aminomethyl)benzene are also of high interest.

In the US patent application US2004/0054219 a production process for trimellitic acid is disclosed wherein pseudocumene is oxidized to obtain a reaction mixture of dimethyl benzoic acid, dimethyl benzyl alcohol and dimethyl benzaldehyde which is further oxidized to trimellitic acid.

A similar process is disclosed in US 2011/0112323, which refers to the oxidation of dimethyl benzaldehyde or derivates thereof to produce trimellitic acid.

In US20165/0264506 the trimellitic acid is an intermediate product for the production of terephthalic acid wherein reductive coupling of two molecules of propionic acid or propionic acid derivatives is carried out.

Although, these documents describe processes for the production of the specific tri-methylbenzene derivative trimellitic acid, there is still the need to provide a process which can be used for producing various trifunctional aromatic molecules.

In particular, none of these documents teaches that furan derivatives, in particular diformylfuran, are good starting materials for the production of these trifunctional aromatic molecules.

In previous studies, the inventors of the present application have found that cyclic ketals of furfural surprisingly react with acrylonitrile thereby forming the desired Diels-Alder adduct. In further reaction stages, the cyclic ketal can be converted back into the desired aldehyde substituent which, if required, can be further reacted to other substituents. This finding is particularly surprising when considering that the dialkyl-ketal derivative of furfural does not form a Diels-Alder adduct with ethylene derivatives. Ketals are known derivatives of aldehydes from which the desired aldehyde can easily be obtained by removing the alcohol. However, when reacting the diethyl-ketal of furfural with acrylonitrile, only traces of the Diels-Alder adduct, the oxanorbornene were observed. During the investigations, the present inventors additionally found that cyclic ketals of furfural surprisingly react with only certain ethylene derivatives. It was, for example, found that cyclic ketals of furfural do not react with allyl amines and acryl amides. Only acrylonitrile and fumaronitrile smoothly reacted in the Diels-Alder condensation reaction. These studies are described in detail in PCT/CN2015/096821, incorporated herein by reference.

The inventors have been now found that by using cyclic ketals of diformylfuran with acrylonitrile the desired Diels-Alder adduct can be also obtained. This Diels-Alder adduct is an intermediate product for the production of cyano-terephthalaldehyde derivatives, which are again good starting materials for the production of various trifunctional aromatic molecules, in particular 1,2,4-dimethyl benzene derivatives such as trimellitic acid or 1,2,4-tri(aminomethyl) benzene.

The present invention therefore relates to a process for the preparation of tri-methyl benzene derivatives from diformylfuran, in particular to a process for the preparation of a compound of Formula (I)

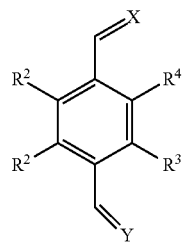

wherein
X and Y independently are optionally substituted heteroatoms;
each $R^2$ independently is H, alkyl, alkenyl or aryl;
$R^3$ and $R^4$ independently are H or —CN, provided that at least one of $R^3$ and $R^4$ is —CN;
a) which comprises dehydration/aromatization of a compound of the Formula (II)

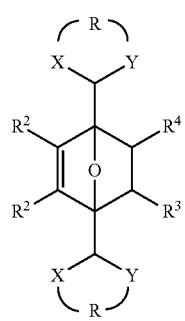

wherein,
X, Y, R, $R^2$, $R^3$, $R^4$ are defined as above and
R is a $C_{1-4}$ alkylene group which may optionally be substituted with one or more $R^1$;
wherein $R^1$ is a linear, branched and/or cyclic, saturated or unsaturated hydrocarbon group which optionally bears one or more functional groups to obtain a compound of the Formula (III)

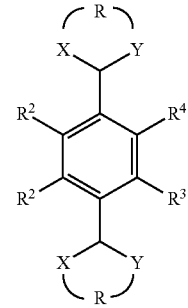

wherein X, Y, R, $R^2$, $R^3$, $R^4$ are defined as above;
followed by deprotection of the compound of Formula (III);
or
b) which comprises carrying out the dehydration/aromatization and the deprotection of the compound of Formula (II) in a single step.

The compound of Formula (II)

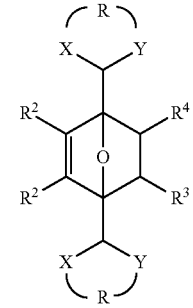

wherein
X and Y independently are optionally substituted heteroatoms;
R is a $C_{1-4}$ alkylene group which may optionally be substituted with one or more $R^1$;
$R^1$ is a linear, branched and/or cyclic, saturated or unsaturated hydrocarbon group which optionally bears one or more functional groups;
$R^2$ independently is H, alkyl, alkenyl or aryl;
$R^3$ and $R^4$ independently are H or —CN, provided that at least one of $R^3$ and $R^4$ is —CN;
is preferably produced by reacting a compound of the Formula (VI), a diformylfuran derivative,

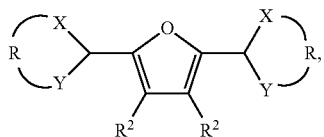

wherein X, Y, R, $R^2$ are defined as above with a compound of the Formula (VII) or (VII')

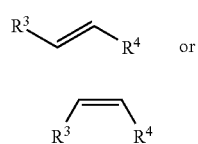

wherein $R^3$ and $R^4$ are defined as above.

The diformylfuran derivative of Formula (VI) can for example be produced by oxidation of 5-hydroxymethyl-2-furfural (HMF) as described for example in Applied Catalysis A, Vol. 456, pages 44-50.

In the diformylfuran derivative of Formula (VI) the aldehyde residue of diformylfuran is present as cyclic ketal. However, the present invention is not limited to diformylfuran and its cyclic ketal derivative but also includes diformylfuran derivatives comprising heteroatoms other than O. Therefore, X and Y in the compound of Formula (VI) are independently of each other optionally substituted heteroatoms, such as O, S and N.

In this context, "optionally substituted" defines that the heteroatom may bear a substituent, if required. If the heteroatom cannot bear any further substituent, no substituent is present. For example, if the heteroatom is O or S, there is no substituent at the heteroatom. However, if the heteroatom is N, then X and Y may be —NH— or —N(substituent)-. This substituent has the same meaning as $R^1$. Thus, X and Y are preferably independently selected from —O—, —S—, —NH—, and —N($R^1$)—, more preferably from —O— and —S—. Most preferably, X and Y are both O or both S.

In the diformylfuran derivative of Formula (VI), R is a $C_{1-4}$ alkylene group, preferably a $C_{2-4}$ alkylene group, more preferably, a $C_{2-3}$ alkylene group, most preferably a $C_2$ alkylene group. This alkylene group may optionally be substituted with one or more $R^1$ substituents. $R^1$ as a linear, branched and/or cyclic, saturated or unsaturated hydrocarbon group which optionally bears one or more functional groups. Such hydrocarbon groups include all chemical moieties comprising carbon atoms, preferably from 1 to 24 carbon atoms besides the required number of hydrogen atoms. Examples of linear, branched, and/or cyclic, saturated or unsaturated hydrocarbon groups are alkyl, alkenyl, alkynyl, aromatic groups, etc. The hydrocarbon group may optionally bear one or more functional groups which means that the hydrocarbon group may contain one or more heteroatoms, such as O, N and S, or functional groups, such as —CO— or —COO—. Furthermore, the hydrocarbon group may be substituted with functional groups, such as nitro, nitroso, sulfo, sulfonate, cyano, cyanato, thiocyanato, amino, hydroxyl, carboxyl, etc.

Representative examples of $R^1$ will now be explained in more detail, thereby also providing definitions of certain terms which are applicable throughout the present specification and in particular also for all other substituents, if not defined otherwise.

The term "alkyl" as used herein refers to a linear, branched, or cyclic saturated hydrocarbon group typically although not necessarily containing 1 to about 24 carbon atoms, preferably 1 to about 12 carbon atoms, or 1 to about 6 carbon atoms, 1 to about 3 carbon atoms. Certain embodiments provide that the alkyl is methyl, ethyl, n-propyl, isopropyl, n-butyl, isobutyl, tert-butyl, octyl, decyl, or the like, as well as cycloalkyl groups such as cyclopentyl, cyclohexyl or the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and include "heteroatom-containing alkyl" and "heteroalkyl," which terms refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms.

The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound by a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxyphenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl", and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo" and "halogen" are used in the conventional sense to refer to a chloro, bromo, fluoro, or iodo substituent.

The term "heteroatom-containing" as in a "heteroatom-containing group" refers to a hydrocarbon molecule or molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl", "substituted aryl", and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups, such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl —($C_5$)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH aryl), di-($C_5$-$C_{24}$ aryl)-substituted thiocarbamoyl ((CO)—N($C_5$-$C_{24}$ aryl)z), di-N—($C_1$-$C_{24}$ alkyl), N—($C_5$-$C_{24}$ aryl)-substituted thiocarbamoyl, carbamido (—NH—(CO)—NH2), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR═NH where R═hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (CR═N(alkyl), where R═hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R═hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$OH), sulfonate ($SO_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl-$SO_2$—N(H) alkyl), $C_1$-$C_{24}$ dialkylaminosulfonyl-$SO_2$—N(alkyl)$_2$, $C_5$-$C_{24}$ arylsulfonyl (—$SO_2$-aryl), boryl (—$BH_2$), borono (B(OH)$_2$), boronato (—B(OR)$_2$ where R is alkyl or aryl), phosphono (—P(O)(OH)$_2$), phosphonato (P(O)(O)$_2$), phosphinato (P(O)(O—)), phospho (—$PO_2$), and phosphine (—$PH_2$); and the moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Where substituents are described as "substituted" or "optionally substituted," these Fn substitutions preferably comprise halo, hydroxyl, $C_1$-$C_3$ alkoxy, $C_1$-$C_6$ alkylcarbonyl (CO—alkyl), $C_2$-$C_{24}$ alkoxycarbonyl ((CO)—O-alkyl), carboxy (—COOH), carbamoyl (—(CO)—$NH_2$), mono-($C_1$-$C_6$ alkyl)-substituted carbamoyl (—(CO)NH($C_1$-$C_6$ alkyl)), di-($C_1$-$C_6$ alkyl)-substituted carbamoyl (—(CO)—N($C_1$-$C_6$ alkyl)$_2$), cyano(—C≡N), cyanato (—O—C≡N), thiocyanato (—S—C≡N), formyl (—(CO)—H), amino (—$NH_2$), mono-($C_1$-$C_6$ alkyl)-substituted amino, or di-($C_1$-$C_6$ alkyl) substituted amino.

By "functionalized" as in "functionalized alkyl", "functionalized olefin", "functionalized cyclic olefin", and the like, is meant that in the alkyl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups such as those specifically enumerated above. Analogously, the above-mentioned groups may be further substituted with one or more functional groups such as those specifically enumerated.

In a preferred embodiment of the present invention R is a $C_2$ or $C_3$ alkylene group which is unsubstituted or substituted with one or two, preferably two lower alkyl, preferably methyl or ethyl, more preferably methyl. Preferred examples for R are —$CH_2$—$CH_2$—, —$CH_2$—$CH_2$—$CH_2$—, —CH($CH_3$)—CH($CH_3$)— and —$CH_2$—C($CH_3$)$_2$—$CH_2$—.

In the diformylfuran derivative of Formula (VI), $R^2$ independently is H, alkyl, alkenyl or aryl, as defined above. Preferably, $R^2$ independently is H or alkyl, more preferably H or $C_{1-4}$ alkyl, more preferably H or $C_{1-3}$ alkyl, even more preferably H or $C_{1-2}$ alkyl, most preferably H or methyl. In a further preferred embodiment, $R^2$ is H.

Certain embodiment of the diformylfuran derivatives of Formula (VI) are the following compounds:

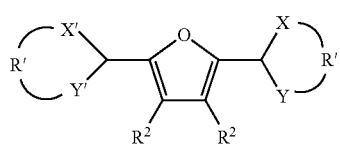

wherein
X' and Y' are both O or S; and
R' is $C_2$ or $C_3$ alkylene being optionally substituted with one or two $C_{1-4}$ alkyl (preferably methyl);

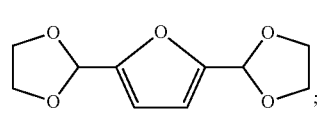

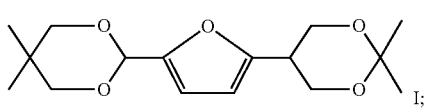

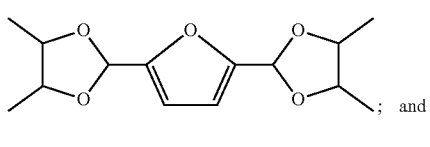

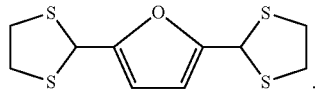

The diformylfuran derivatives of Formula (VI) can be obtained for example by reacting diformylfuran with ethylene glycol, substituted ethylene glycol or any other suitable dialcohol. This reaction, which also constitutes a protection of the aldehyde function of the diformylfuran in the form of a cyclic ketal, is known to the person skilled in the art. The protection reaction can, for example, be carried out in a suitable organic solvent, such as cyclohexane, using a suitable catalyst, such as A15 amberlyst resin. For example, a diformylfuran derivative of Formula (VI), which is 2,5-bis (1,3-dioxolan-2-yl)furan can be obtained quantitatively by reacting diformylfuran with ethylene glycol.

According to the invention it has been found that the diformylfuran derivative of Formula (VI) surprisingly reacts with a diene resulting in the Diels-Alder adduct of Formula (II) although diformylfuran itself and the dialkyl-ketal derivative of diformylfuran do not form a Diels-Alder adduct with ethylene and its derivatives.

Therefore, for the production of the Diels-Alder condensation adduct of Formula (II) a diformylfuran derivative of Formula (VI) is reacted with the ethylene derivative of Formula (VII).

The ethylene derivative of Formula (VII) or (VII') bears two substituents, $R^3$ and $R^4$. These substituents independently are H or —CN, provided that at least one of $R^3$ and $R^4$ is —CN. Thus, the ethylene derivative of Formula (VII) or (VII') bears at least one substituent. In one embodiment, $R^4$ is H and $R^3$ is —CN. Alternatively, $R^3$ and $R^4$ may both be —CN. If both, $R^3$ and $R^4$ are —CN, the ethylene derivative includes the cis- and the trans-isomer of fumaronitrile.

The Diels-Alder condensation reaction between the compound of Formula (VI) and the compound of Formula (VII) or (VII') can be carried out under usual Diels-Alder conditions known to the person skilled in the art. Depending on the specific derivatives employed, the condensation reaction can be carried out in the presence or without any catalysts and also with or without any solvent. The reaction can be carried out at any suitable temperature of from about 10 to about 120° C., preferably from about 20 to about 100° C., more preferably from about 20 to about 80° C., for a time sufficient to convert the starting compounds into the desired Diels-Alder adduct, such as about 2 or 5 seconds to about 6 days, preferably about 3 hours to about 4 days, more preferably about 12 hours to about 4 days, such as about 44 hours or about 24 hours. The reaction can be carried out at ambient pressure or increased pressure. Advantageously, the reaction is carried out at ambient pressure, such as about 1000 hPa or at a pressure of up to about 10000 hPa, preferably up to about 5000 hPa, more preferably up to about 2000 hPa.

Advantageously, the Diels-Alder reaction is conducted in the presence of a catalyst, in particular known Diels-Alder catalysts. These catalysts include Lewis acids, e.g. aluminum, boron, zinc, hafnium, or iron compounds, such as $AlCl_3$, $Al(Et)Cl_2$, $Al(Et)_2Cl$, $BF_3$, $B(Ac)_3$, $ZnCl_2$, $ZnBr_2$, $Zn(Ac)_2$, $ZnI_2$, $CuCl_2$, $Sc(OTf)_3$, $Bi(OTf)_3$ and $BiCl_3$, $FeCl_3$, $Fe(Ac)_3$, $FeCl_2$ and $Fe(Ac)_2$, Brønsted acids, such a inorganic mineral acids, e.g. sulphuric acid, phosphoric acid, nitric acid, hydrobromic acid or hydrochloric acid, and organic acids, such as methane sulphonic acid, p-toluenesulphonic acid, or carboxylic acids. Diels-Alder catalysts also include halides of tin or titanium, such as $SnCl_4$ and $TiCl_4$. Alternatively, activated carbon, silica, alumina, silica-alumina, zirconia or zeolites may be used. Carbon, silica, alumina, silica-alumina, zirconia and zeolites may be used as such, but they may also be used as support for a catalytically active metal or metal compound. Such metals or metal compounds suitably include alkali metals, alkaline earth metals, transition metals, noble metals, rare earth metals. The catalysts can be acidic, e.g. by treating supports with phosphoric acid, or by ion exchange of zeolites to render them into their acidic form. The catalyst can be an acid catalyst. Examples of solid catalysts include amorphous silica-alumina, zeolites, preferably zeolites in their H-form, and acidic ion exchange resins. Other suitable catalysts that are liquids or that may be dissolved in the appropriate solvent to yield a homogeneous catalyst environment, include organic and inorganic acids, such as alkane carboxylic acid, arene carboxylic acid, sulphuric acid, phosphoric acid, hydrochloric acid, hydrobromic acid and nitric acid.

The Diels-Alder condensation reaction between the compound of Formula (VI) and the compound of Formula (VII) or (VII') results in the oxanorbornene derivative of Formula (II). Depending on the starting compounds used, the obtained oxanorbornene may be obtained as different isomers, such as endo- or exo-isomers or mixtures thereof. All possible isomers and mixtures thereof are included within the scope of the present invention.

The oxanorbornene derivative of Formula (II), in particular of Formula (II'), constitutes a valuable intermediate in the preparation of other chemical compounds, such as a compound of Formula (III), in particular of Formula (III'),

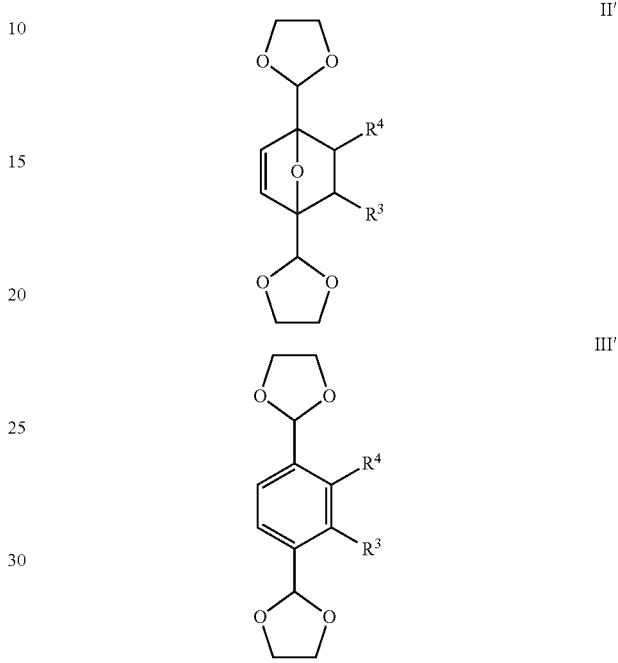

wherein $R^3$ and $R^4$ independently are H or —CN, provided that at least one of $R^3$ and $R^4$ is —CN, which is also a valuable intermediate for the preparation of other chemical compounds.

Both intermediates (II)/(II') and (III)/(III') can be converted to the compound of Formula (I), in particular to the cyano-terephthalaldehyde according to Formula (I'), as described in the following reaction scheme (showing a preferred example of the process according to the invention):

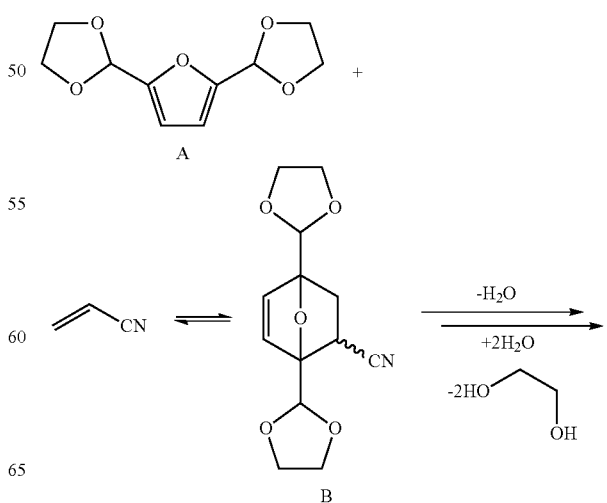

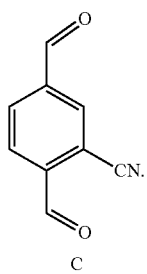

C

The aromatization and deprotection of the compound of Formula (II)/(II') can be carried out in a single step as described above. Alternatively, the desired compound of Formula (I)/(I') can be obtained in a two-step process through the intermediate of the Formula (III)/(III'). This alternative route is shown in the following reaction scheme which again exemplifies the reaction using preferred compounds:

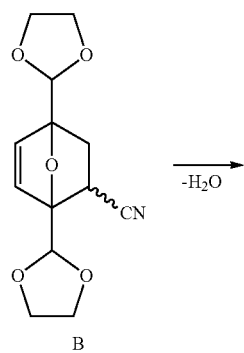

If desired, the compound of Formula (I) obtained in the process according to the invention may be further converted into other chemical compounds, such as for example mono-cyanoterephthalic acid, 2,3-dicyanoterephthalic acid, aminomethylterephtalic acid, 2,3-diaminomethylterephtalic acid, trimellitic acid or 1,2,4-tri(aminomethyl)benzene.

In a preferred embodiment of the invention the desired product is a compound according to Formula (IV), preferably a 1,2,4-tri(aminomethyl)benzene,

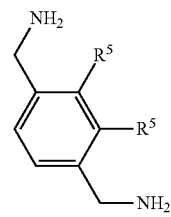

IV wherein $R^5$ independently is H or $CH_2$—$NH_2$, provided that at least one of $R^5$ is —$CH_2$—$NH_2$, which can be obtained by nitrile hydrogenation of the cyano moiety and reductive amination of the aldehyde moiety of compound according to Formula (I). The nitrile hydrogenation and reductive amination can be conducted simultaneously, for example by reacting cyanoterephthalic acid in a solution of $NH_3$ in methanol (ratio $NH_3$/3-cyanobenzaldehyde about 19), at 100° C., 50 bar of hydrogen with Co Raney as catalyst. Alternatively, nitrile hydrogenation and reductive amination can be conducted in a multi-step process as schematically shown in the following reaction scheme

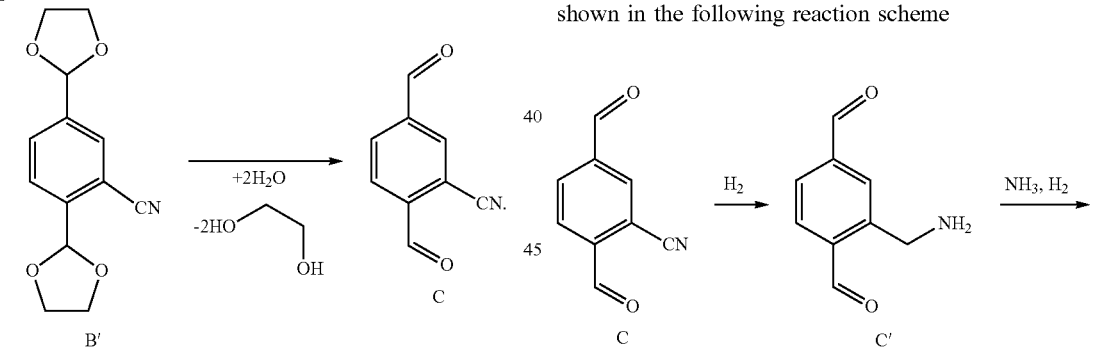

The reaction conditions for aromatization and deprotection of the compound of Formula (II) are well known to a person skilled in the art. It was, however, surprisingly found that the aromatization reaction of the compound of Formula (II) requires basic reaction conditions, for example in the presence of a methoxide or hydroxide, such as sodium methoxide or sodium hydroxide. For example, the aromatization reaction can be conducted in quantitative yield using sodium methoxide in DMSO at a temperature of 100° C. for about 1 hour. Alcohols, such as methanol and ethanol are other suitable solvents.

Preferably, the compound of Formula (II) is obtained by the above described process using diformylfuran and in particular the cyclic ketal derivative of diformylfuran having the Formula (VI) as starting material.

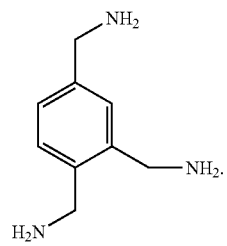

In another preferred embodiment of the invention the compound of Formula (I) is converted into to a tri-methyl benzene derivative of the Formula (V)

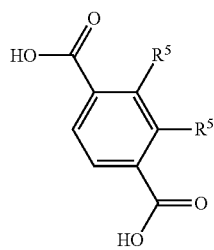

wherein R⁵ independently is H or —CO₂H, provided that at least one of R⁵ is —CO₂H; in particular converted into trimellitic acid having the formula (V'), and which can be obtained by simultaneous or subsequent oxidation and hydrolysis of a compound of Formula (I')

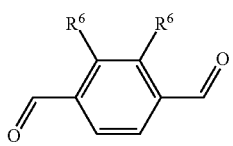

wherein R⁶ independently is H or —CN, provided that at least one of R⁶ is —CN; which is obtained by the process of the invention.

The oxidation and hydrogenation of the compound of Formula (I)/(I') can be carried out by any suitable process known in the art. For example, in order to produce trimellitic acid, 2-cyanoterephthalic acid is added to sodium hydroxide solution and refluxed at 115° C. for 5 hours. Afterwards the reaction solution is acidified to pH 1 by sulfuric acid to obtain trimellitic acid, as shown in the following reaction scheme

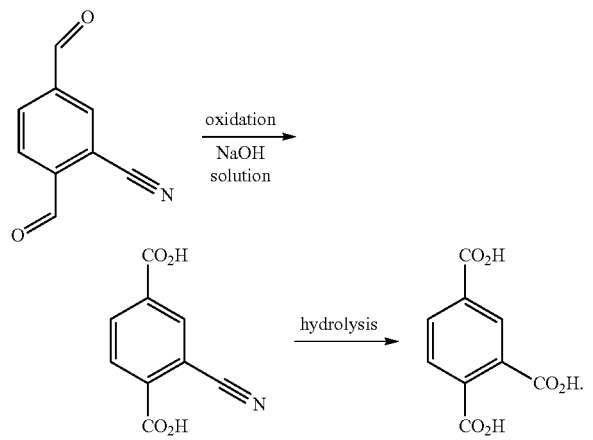

The oxidation and hydrolysis of the compound of Formula (I)/(I') to obtain compound of Formula (V)/(V') can be carried out in a single step as described above. For example, trimellitic acid having Formula (V') can be obtained by adding potassium peroxymonosulfate (Oxone) as oxidant to a solution of the compound of formula (I') in dimethylformamide under stirring at room temperature for 5 hours.

In a further embodiment of the present invention, the process for the production of the compound of Formula (I) can be carried out in a single step as one pot reaction.

In particular the compounds of Formula (II') and (III') are novel intermediates for the above describe process and products thereof.

Should the disclosure of any patents, patent applications, and publications which are incorporated herein by reference conflict with the description of the present application to the extent that it may render a term unclear, the present description shall take precedence.

The present invention will now be illustrated by the following examples, which are not intended to be limiting.

EXAMPLE 1

Production of 2,5-bis(1,3-dioxolan-2-yl)furan

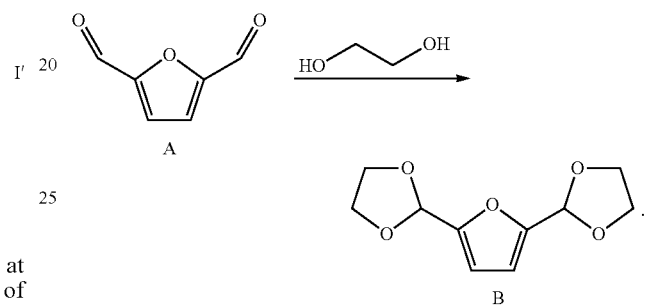

3 g of diformylfuran (DFF) and 50 mg of Amberlyst 15 are suspended in 80 mL of toluene and 9 g of ethylene glycol. The mixture is refluxed in a Dean-Stark apparatus for 4 h. After filtration of Amberlyst, 80 mL of ethyl acetate is added and the organic phase is washed 3 times with 30 mL of water. The organic phase is dried over MgSO₄ and evaporated to get a near pure product.

EXAMPLE 2

Diels-Alder Reaction of
2,5-bis(1,3-dioxolan-2-yl)furan and acrylonitrile

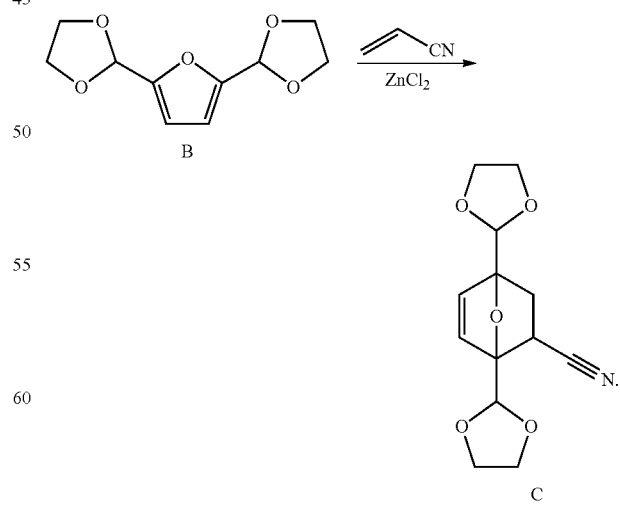

In a carousel tube fitted with a PTFE septum screw cap, 2,5-bis(1,3-dioxolan-2-yl)furan (1.87 g; 8.81 mmol) was weighted. Then, acrylonitrile (2.33 g; 44.0 mmol) and ZnCl$_2$ (281 mg; 2.06 mmol) were added. The reaction mixture was stirred at 60° C. during 43 h. The conversion is 87% to an endo/exo mixture of adducts C. The reaction mixture was concentrated in vacuo. This crude product was purified by flash chromatography (silica gel, EtOAc/cyclohexane) to afford 1.64 g of expected adducts (1.14 g endo and 0.50 g exo) as a slight yellow solids, global isolated yield is 70%.

EXAMPLE 3

Conversion of Diels-Alder Adducts of Previous Example to 2,5-bis(1,3-dioxolan-2-yl)benzonitrile

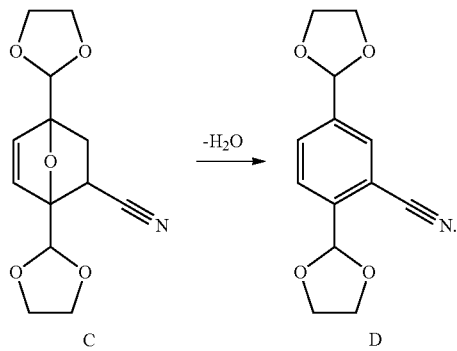

In a carousel tube fitted with a PTFE septum screw cap, endo adduct C (1.0 g; 3.77 mmol), dimethyl sulfoxide (5 ml) and sodium methoxide solution (25 wt. % in methanol; 169 mg; 0.75 mmol) will be charged. The reaction mixture will be stirred at 100° C. during 1 h.

After cooling, the crude product will be diluted with dichloromethane (20 ml). The mixture will be washed with water (10 ml). The aqueous phase will be extracted with dichloromethane (20 ml) and the organic phase will be washed with water (10 ml, 3 times). After drying (MgSO$_4$), the solvent will be evaporated to afford 887 mg of an oily liquid (93%).

EXAMPLE 4

Deprotection of 2,5-bis(1,3-dioxolan-2-yl)benzonitrile to 2,5-Diformylbenzonitrile

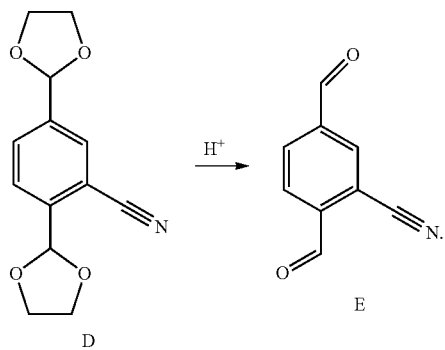

To a stirred solution of 2,5-bis(1,3-dioxolan-2-yl)benzonitrile (200 mg; 0.81 mmol) in THF (10 ml), 1N HCl solution (10 ml) will be added at room temperature. The mixture will be heated at 80° C. for 1 h and cooled to room temperature. The reaction mixture will be extracted with chloroforme (10 ml, 3 times). The combined chloroform solution will be dried (anhydrous MgSO$_4$), filtered and evaporated under reduced pressure to give 126 mg (98%) of 2,5-Diformylbenzonitrile.

EXAMPLE 5

Oxidation of 2,5-Diformylbenzonitrile to 2-cyanoterephthalic acid

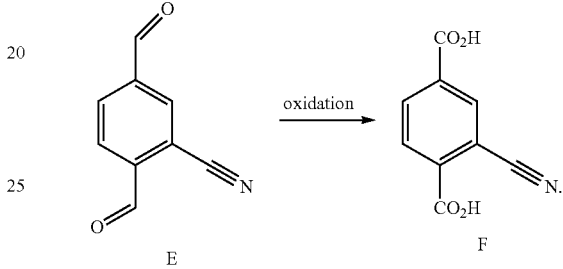

31.8 g (200 mmol) of 2,5-Diformylbenzonitrile, 80 g of dioxane, 35.2 g of sodium hydrogen carbonate, and 200 g of water will be mixed with stirring. 410 g of an aqueous 13.5% by weight sodium hypochlorite solution adjusted to a pH of 9 will be added dropwise over 1 hour while maintaining the internal temperature of the reaction system at 50° C. or less, and the resulting mixture will be stirred for 1 additional hour. Then, 7.2 g of urea will be added and the resulting mixture will be stirred for 20 minutes. Furthermore, 24 g of 98% by weight sulfuric acid and 300 g of water will be added. Precipitated crystals will be formed; they will be filtered, washed with water, and dried to obtain about 35 g (yield: about 92%) of 2-cyanoterephthalic acid. The purity will be 98% or more.

EXAMPLE 6

Hydrolysis of 2-cyanoterephthalic acid to trimellitic acid

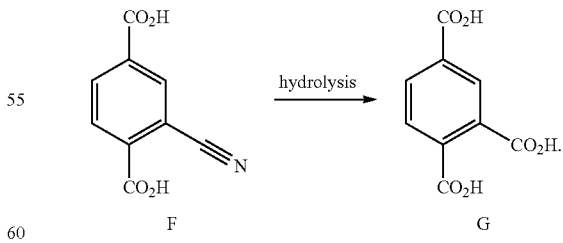

6.5 g (34 mmol) of 2-cyanoterephthalic acid will be added to a solution of NaOH (2.93 g) in water (26 g). The resulting solution will be heated to reflux (115° C.) for 5 hours. After cooling, 70 ml of water will be added and the solution will be acidified to pH=1 by dropwise addition of 95% sulfuric acid. A white solid precipitate will be formed. The white solid precipitate will be filtrated and washed 3 times with 10 ml of water. After drying (60° C., 10 mbar, 2 h), 6.86 g of trimellitic acid (96% yield) will be obtained.

EXAMPLE 7

Production of 2,5-bis(1,3-dioxolan-2-yl)furan

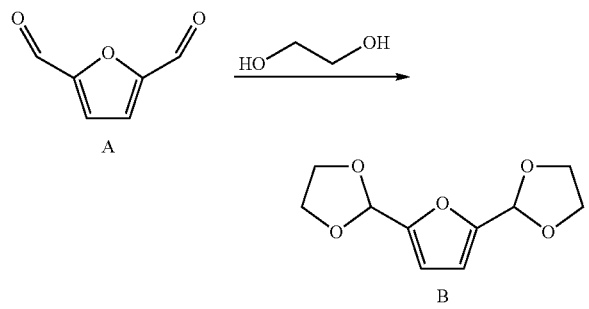

A suspension of diformylfuran (12 g, 96.7 mmol) in toluene (200 ml) is taken in a round bottomed flask with Dean-Stark apparatus. Ethylene glycol (35 g, 563 mmol) and Amberlyst-15H (250 mg) are added to the reaction mixture and the reaction mixture is left refluxing overnight. The reaction mixture is allowed to cool down to room temperature, and filtered to remove acid catalyst. The filtrate is diluted with ethyl acetate (200 ml). The organic phase is washed with sodiumbisulphite solution (3 times) and finally with water. The organic phase is dried over anhydrous $Na_2SO_4$. The filtrate is concentrated and dried to obtain 16 g (yield: 78%) of 2,5-bis(1,3-dioxolan-2-yl)furan.

The product was characterized by NMR spectroscopy.

$^1$H NMR (400 MHz, $CDCl_3$): 6.40 (2H, s), 5.93 (2H, s), 4.12-3.98 (8H, m).

EXAMPLE 8

Diels-Alder Reaction of 2,5-bis(1,3-dioxolan-2-yl)furan and acrylonitrile

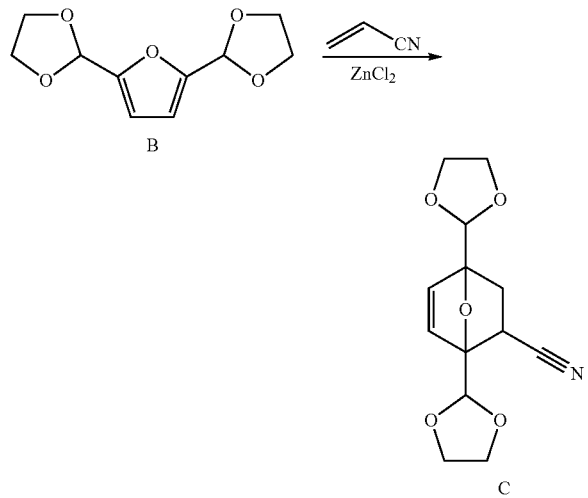

2,5-bis(1,3-dioxolan-2-yl)furan (10 g, 47.13 mmol) was taken in a high pressure tube. Added acrylonitrile (12 ml, 183.18 mmol) and $ZnCl_2$ (1 g, 7.7 mmol) to the tube and the tube was tightly closed. The reaction mixture was left stirring at 65° C. for 48 h. Complete consumption of the starting materials was confirmed by Thin layer chromatography (eluent: 50% EtOAc/cyclohexane). The reaction mixture was cooled down to room temperature, and diluted with dichloromethane (250 ml). The organic phase was washed with $NaHCO_3$ solution and water. Finally the organic phase was dried over anhydrous $Na_2SO_4$. The filtrate was concentrated and dried. The crude mixture was purified by column chromatography to isolate the endo/exo mixture of Diels-Alder product (9.6 g, yield: 77%).

The product was characterized by NMR spectroscopy.

$^1$H NMR (400 MHz, $CDCl_3$): 6.58 (0.72H, d, J=6 Hz), 6.55 (0.72H, d, J=6 Hz), 6.45 (0.28H, dd, J=0.8 & 6 Hz), 6.28 (0.28H, d, J=5.6 Hz), 5.44 (0.28H, d, J=0.7 Hz), 5.35 (0.72H, s), 5.29 (0.28H, s), 5.22 (0.72H, s), 4.14-3.92 (8H, m), 3.15 (0.72H, dd, J=4 &9.6 Hz), 2.65 (0.28H, dd, J=4 & 8 Hz), 2.43 (0.72H, dd, J=9.6 & 11.6 Hz), 2.25 (0.28H, dd, J=4 & 11.6 Hz), 1.94 (0.28H, dd, J=8.4 & 11.6 Hz), 1.68 (0.72H, dd, J=4 & 11.6 Hz).

$^{13}$C NMR (100 MHz, $CDCl_3$): 137.6/137.5, 133.7, 133.7, 120.1, 119.7, 101.4, 101.4, 101.1, 101, 91.3, 91.2, 91.1, 90.8, 66.3, 66.2, 65.9, 65.9, 65.8, 65.8, 33.9, 33.8, 31.1, 27.9.

EXAMPLE 9

Conversion of Diels-Alder Adducts of Previous Example to 2,5-bis(1,3-dioxolan-2-yl)benzonitrile

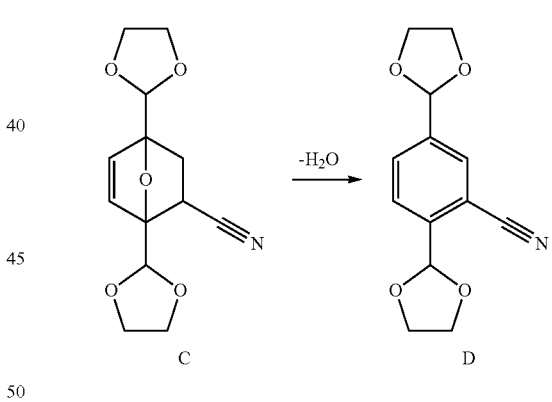

A solution of Diels-Alder product mixture (6 g, 22.6 mmol) in dimethyl sulfoxide (40 ml) was taken in a round bottomed flask, and added grinded powder of KOH (2.5 g, 44.56 mmol) to the solution. The suspension was left stirring at room temperature for 2 h. Complete consumption of the starting material was confirmed through Thin layer chromatography (eluent: 40% EtoAc/cyclohexane). Diluted the reaction mixture with dichloromethane (200 ml). The organic phase was washed with water (3-4 times). The organic phase was dried over anhydrous $Na_2SO_4$ and filtered. The filtrate was concentrated and dried to obtain the pure product (5.1 g, yield: 91%). The product was used for the next step without any further purification.

The product was characterised by NMR spectroscopy.

$^1$H NMR (400 Hz, $CDCl_3$): 7.83 (1H, d, J=4 Hz), 7.69 (1H, dd, J=4 & 8 Hz), 7.62 (1H, d, J=8 Hz), 5.98 (1H, s), 5.83 (1H, s), 4.23-4.05 (8H, m). $^{13}$C NMR (100 MHz, CDCl$_3$): 141.9, 140.6, 131.9, 130.9, 128.1, 117.1, 111.6, 102.2, 101.9, 66.1, 65.6.

EXAMPLE 10

Deprotection of 2,5-bis(1,3-dioxolan-2-yl)benzonitrile to 2,5-Diformylbenzonitrile

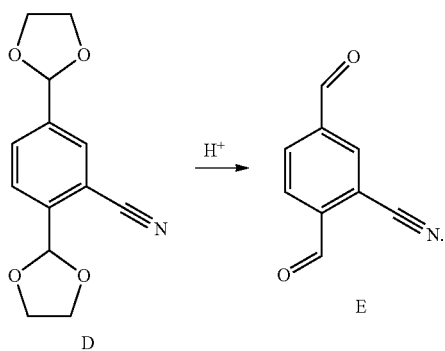

A solution of 2,5-bis(1,3-dioxolan-2yl)benzonitrile (4.9 g, 19.82 mmol) in acetone (60 ml) was taken in a round bottomed flask. Diluted HCl (2-3N aqueous solution, 60 ml) was added to the reaction mixture and the reaction mixture was left stirring at room temperature for 5-6 h. Concentrated the reaction mixture under reduced pressure, and extracted the organic compounds into dichloromethane (3×60 ml). The combined organic phase was further washed with water and dried over anhydrous Na$_2$SO$_4$. The filtrate was concentrated and dried to obtain pure product (2.6 g, yield: 83%).

The product was characterised by NMR spectroscopy.

$^1$H NMR (400 MHz, CDCl$_3$): 8.33 (1H, dd, J=0.4 & 1.6 Hz), 8.27 (1H, ddd, J=0.5, 1.5 & 8 Hz), 8.23 (1H, d, J=8 Hz). $^{13}$C NMR (100 MHz, CDCl$_3$): 189.4, 188.0, 140, 139.8, 134.9, 133.8, 130.6, 115.2, 114.9.

EXAMPLE 11

Oxidation of 2,5-Diformylbenzonitrile to Trimellitic Acid

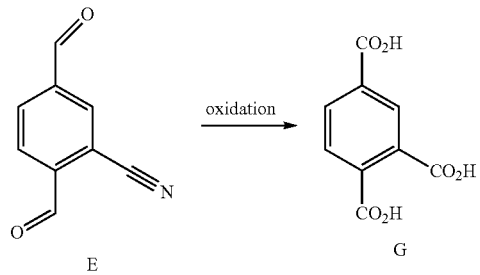

A solution of 2,5-Diformylbenzonitrile (1.4 g, 8.8 mmol) in dimethylformamide (20 ml) was taken in a round bottomed flask. Added oxone (potassium peroxymonosulfate) (5.4 g, 17.57 mmol) to the reaction mixture and the suspension was left stirring at room temperature for 5-6 h. Complete consumption of the starting material was confirmed by Thin layer chromatography. The reaction mixture was filtered to remove the precipitate (most of the inorganic salt). Distilled out dimethylformamide from the filtrate at reduced pressure and dried the residual solid (about 2 g). The residual solid was characterized by Liquid Chromatography Mass Spectroscopy (LCMS) and isolated trimellitic acid after purification by reverse phase column chromatography. Trimellitic acid was isolated after column chromatography.

The product was characterised by NMR spectroscopy.

$^1$H NMR (400 MHz, DMSO-d6): 8.22 (1H, d, J=1.5 Hz), 8.11 (1H, dd, J=1.7 & 8 Hz), 7.56 (1H, d, J=8 Hz).

$^{13}$C NMR (100 MHz, DMSO-d6): 168.4, 167.5, 166, 137.4, 132.4, 132.2, 131.8, 129.5, 128.7.

The invention claimed is:

1. A process for the preparation of a compound of Formula (I)

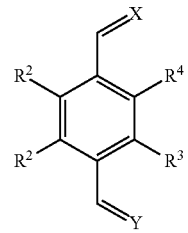

wherein

X and Y independently are optionally substituted heteroatoms;

each $R^2$ independently is H, alkyl, alkenyl or aryl;

$R^3$ and $R^4$ independently are H or —CN, provided that at least one of $R^3$ and $R^4$ is —CN; the process comprising a.) dehydration/aromatization of a compound of the Formula (II)

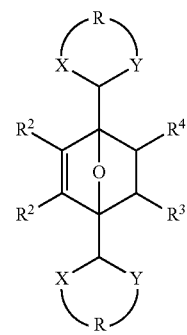

wherein

X and Y independently are optionally substituted heteroatoms;

R is a $C_{1-4}$ alkylene group which may optionally be substituted with one or more $R^1$;

$R^1$ is a linear, branched and/or cyclic, saturated or unsaturated hydrocarbon group which optionally bears one or more functional groups;

$R^2$ independently is H, alkyl, alkenyl or aryl; and $R^3$ and $R^4$ independently are H or —CN, provided that at least one of $R^3$ and $R^4$ is —CN;

to obtain a compound of the Formula (III)

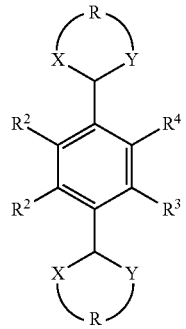

wherein X, Y, R, $R^2$, $R^3$ and $R^4$ are defined as above;

followed by deprotection of the compound of Formula (III);

or b.) carrying out the dehydration/aromatization and the deprotection of the compound of Formula (II) in a single step.

2. The process according to claim 1, wherein X and Y are O or X and Y are S.

3. The process according to claim 1, wherein R is —$CH_2$—$CH_2$—, $CH_2$—$CH_2CH_2$—, —$CH(CH_3)$—$CH(CH_3)$— or $CH_2$—$C(CH_3)_2$—$CH_2$—.

4. The process according to claim 1, wherein $R_2$ is H.

5. The process according to claim 1, wherein X and Y are O and R is —$CH_2$—$CH_2$—.

* * * * *